United States Patent [19]

Michetti

[11] Patent Number: 5,525,588
[45] Date of Patent: Jun. 11, 1996

[54] COSMETIC COMPOSITION

[75] Inventor: Deborah A. Michetti, East Haven, Conn.

[73] Assignee: Elzabeth Arden Co., New York, N.Y.

[21] Appl. No.: 306,031

[22] Filed: Sep. 14, 1994

[51] Int. Cl.⁶ ........................................... A61K 7/46
[52] U.S. Cl. ........................ 512/4; 514/844; 514/846
[58] Field of Search ........................ 512/4; 514/844, 514/846

[56] References Cited

U.S. PATENT DOCUMENTS

| | | | |
|---|---|---|---|
| 3,681,248 | 8/1972 | Gould et al. | 512/4 |
| 4,346,118 | 8/1982 | Islam | 424/313 |
| 4,677,119 | 6/1987 | Dymicky et al. | 514/541 |
| 5,310,556 | 5/1992 | Ziegler | 514/844 |
| 5,362,482 | 11/1994 | Yoneyama et al. | 514/844 |
| 5,374,614 | 12/1994 | Behan et al. | 512/4 |

OTHER PUBLICATIONS

Technical Bulletin on Marrix™ SF–dated May 1, 1992.
Opdyke, Chem. Abst; vol. 91, #198715g (1979).
Dymicky et al., Chem. Abst; vol. 102, #61069a (1985).
Benzoni, Chem. Abst., vol. 105, #11,855v (1986).

*Primary Examiner*—James H. Reamer
*Attorney, Agent, or Firm*—Milton L. Honig

[57] ABSTRACT

An oil-in-water emulsion cosmetic composition is provided including a fragrance and a vehicle system noninterfering with the fragrance scent and including water, oil, a thickener and a dialkyl diester of melting point 35°–45° C. The diester is preferably di-$C_{12}$–$C_{15}$ alkyl fumarate.

4 Claims, No Drawings

COSMETIC COMPOSITION

BACKGROUND OF THE INVENTION

1. Field of the Invention

The present invention relates to oil and water emulsions formulated with fragrance, especially a fragrance delivering body lotion.

2. The Related Art

Perfumes are often accompanied in the marketplace by an array of related cosmetics carrying the perfume family trademark. These cosmetics may be eau de toilette, cologne, antiperspirants/deodorants, shaving cream, aftershave balm and body lotions. Ordinarily, fragrances are specifically created for cosmetic products. Not so in the world of the signature perfume entourage product. Here the fragrance must be the same, or at least quite similar, to confirm association of perfume with the entourage product. For instance, Sunflowers®, Red Door®, Chloe Narcisse, Calvin Klein®, Lagerfeld® or Elizabeth Taylor White Diamonds® perfumes would contribute their scent to a name related cosmetic formulation.

One name related product often accompanying a signature perfume is body lotion. Besides the fragrance, these lotions are constituted of oil and water, a thickener and a skinfeel agent. The skinfeel agent must have a suitable melting point, must be odor compatible with the fragrance, contribute to emolliency and assist in promoting phase compatibility between oil and water. The art is continually searching for formulations exhibiting improved performance within the aforedescribed criteria.

Accordingly, it is an object of the present invention to provide an improved cosmetic composition, especially a body lotion with fragrance in a carrier system having improved skinfeel and emolliency properties.

Another object of the present invention is to provide a cosmetic composition, especially a body lotion with fragrance in a carrier system which does not interfere with the scent of the fragrance.

Still another object of the present invention is to provide a cosmetic composition, especially a body lotion with fragrance in a carrier system having good phase compatibility between oil and water components.

These and other objects of the present invention will become more readily apparent from consideration of the following summary and detailed description.

SUMMARY OF THE INVENTION

A cosmetic emulsion composition, especially a body lotion, is provided that includes:

(i) from about 0.5 to about 5% by weight of a fragrance;
(ii) from about 50 to about 95% by weight of water;
(iii) from about 0.1 to about 10% of a thickening agent;
(iv) from about 0.1 to about 40% of an oil; and
(v) from about 0.1 to about 10% of a dialkyl diester having a melting point from about 35° to about 45° C.

DETAILED DESCRIPTION OF THE INVENTION

Emulsions are dispersed systems containing at least two immiscible liquid phases, one of which is dispersed in the form of small droplets throughout the other. Typically, one of the two immiscible liquids in an emulsion is aqueous while the other is an oil. Emulsions may be classified depending on which liquid forms the dispersion medium. An emulsion in which oil is dispersed as droplets throughout the aqueous phase is termed an oil-in-water emulsion. When water is the dispersed phase and an oil is the dispersion medium, a water-in-oil emulsion exists. Whether the aqueous phase or the oil phase becomes the dispersed phase, or is the dispersion medium, depends primarily on the emulsifying agents used in the relative amounts of the two liquid phases. Emulsified lotions contemplated herein are of the oil-in-water type wherein the continuous phase is water.

According to the present invention there is provided a stable oil-in-water emulsion whose components have odor properties which would not interfere with a signature fragrance. Improved hand or skinfeel and good emolliency are other properties exhibited by compositions of the present invention.

An essential element in compositions of this invention is a dialkyl diester with a melting point from about 35° to about 45° C., preferably from 37° to 39° C. Particularly preferred are dialkyl fumarates, most especially di- $C_{12}$–$C_{15}$ alkyl fumarates. The latter material is available from the Heterene Corporation, and through its distributor the Bernel Chemical Co., Inc. of Englewood, N. J. Amounts of the diester will range from about 0.1 to about 10%, preferably from about 0.5 to about 5%, optimally between about 0.8 and 2% by weight.

A thickener will also be present in compositions of this invention. Representative of this group are the polyacrylics, such as polyacrylates crosslinked with allyl sucrose commercially available as Carbopol® 934 from the B. F. Goodrich Company of Akron, Ohio, and polyacrylic acid commercially available as Sythalon N from the Three V Company, Weehawken, N. J. Amounts of the thickener will range from about 0.05 to about 5%, preferably from about 0.1 to about 2%, optimally from about 0.2 to about 0.4% by weight.

Compositions of the present invention will also contain an oil in amounts from about 1 to about 45%, preferably from about 3 to about 30%, optimally from about 5 to about 15% by weight. Oils are organic substances liquid at room temperature (i.e. 20° C.). Oils are useful not only for emollient purposes but may also impart viscosity, tackiness and drag properties. There are several sub-categories of oils which may form a portion of the total amount of oil. These are:

(1) from about 5 to about 90% by weight of the total amount of oil of a $C_1$–$C_6$ alkyl $C_8$–$C_{20}$ fatty acid monoester. Illustrative of this category are isopropyl myristate, methyl myristate, butyl myristate, isopropyl stearate, methyl stearate, butyl stearate, isopropyl oleate, methyl oleate, butyl oleate, isopropyl laurate, isopropyl palmitate and combinations thereof.

(2) from about 5 to about 90% by weight of the total amount of oil of a mono-, di- or tri- glyceride. Illustrative of this category are glyceryl monoisostearate, glyceryl monostearate, glyceryl diisostearate, glyceryl distearate, glyceryl monooleate, caprylic/capric triglyceride, isostearic triglyceride and combinations thereof.

(3) from about 5 to about 90% by weight of the total amount of oil of a volatile or nonvolatile silicone oil. Illustrative of this category are dimethyl polysiloxane, methylphenyl polysiloxane and silicone copolyol. Particularly preferred are dimethicone and cyclomethicone. These materials are commercially available as Dow Corning® Silicone fluid 200 (a methyl polysiloxane) and Dow Corning® 3225C (mixture of dimethicone, cyclomethicone and dimethicone copolyol).

Fatty alcohols and fatty acids having from 10 to 20 carbon atoms may also be present in compositions of this invention. Suitable examples include cetyl alcohol or acid, myristic alcohol or acid, palmitic alcohol or acid, stearic alcohol or acid, isostearic alcohol or acid, oleyl alcohol or acid and combinations thereof. Amounts may range from 0.1 to 10% by weight.

Emulsifiers in amounts from 0.1 to about 10%, preferably from about 1 to about 5% will be present in compositions of this invention. Particularly preferred are $C_8-C_{22}$ alkyl ether phosphates. Illustrative is triceteareth-4 phosphate. Additionally there may be present nonionic, anionic, cationic or amphoteric emulsifying agents, each within the range specified above.

A fragrance blend corresponding to the scent of a commercial signature perfume will also be found in compositions of this invention in amounts ranging from about 0.5 to 5%, preferably from about 1 to about 4% by weight. The term "commercial signature perfume" is intended to mean a fragrance formulation emitting a pleasant odor and sold for such main purpose as a perfume. A fragrance may include such components as $C_{10}-C_{30}$ terpenes, $C_5-C_{50}$ aldehydes, $C_5-C_{50}$ ketones, $C_5-C_{50}$ esters and combinations thereof. The following is a list of illustrative fragrance components:

iso-amyl salicylate,
carvacrol,
clove leaf oil,
ethyl salicylate,
iso-eugenol,
hexyl salicylate,
thyme oil red,
geraniol,
limonene,
6-acetyl-1,1,3,4,4,6-hexamethyl-tetrahydronaphthalene,
p-t-amyl cyclohexanone,
2-n-heptylcyclo-pentanone,
a-iso-methyl ionone,
β-methyl naphthyl ketone,
iso-butyl quinoline,
methyl anthranilate,
o-t-butylcyclohexyl acetate,
diethyl phthalate,
nonanediol-1,3-diacetate,
nonanolide-1,4,
i-nonyl acetate,
i-nonyl formate,
phenylethyl phenyl acetate,
cinnamic alcohol,
dimyrcetol,
hydroxymethyl isopropyl cyclopentane,
tetrahydromuguol,
cedar wood oil,
geranyl phenylacetate,
guaiacwood oil,
linalyl benzoate,
phenyl ethyl alcohol,
dihydromyrcenol,
linalool,
isolongifolanone,
hexyl cinnamic aldehyde,
linalyl acetate,
citronellyl acetate,
phenyl ethyl acetate,
acetyl tributyl citrate,
benzyl salicylate,
isobutyl cinnamate,
linalyl cinnamate,
coumarin,
para-t-butyl cyclohexyl acetate,
acetyl cedrene,
allyl amyl glycolate,
vanillin,
patchouli oil,
bergamot oil,
citronellol, and combinations thereof.

The nomenclature adopted for the components listed above, so far as possible, is that employed by Steffan Arctander in "Perfume and Flavor Chemicals (Aroma Chemicals)" Volume I and II (1969) and the "Perfume & Flavor Materials of Natural Origin" (1960) by the same author.

The compositions of this invention will contain water in amounts from about 50 to about 98%, preferably from about 60 to about 95%, optimally from about 70 to about 90% by weight of the cosmetic compositions.

Humectants of the polyhydric alcohol type may be included in the aqueous phase of compositions according to the present invention. Amounts of the humectant may range from about 0.5 to about 10% by weight of the cosmetic composition. Illustrative of this category are propylene glycol, dipropylene glycol, polyethylene glycol, sorbitol, glycerin and mixtures thereof.

Preservatives are usually incorporated into cosmetic compositions of this invention at levels ranging from 0.01 to 3%, preferably from about 0.3 to about 2%, optimally from about 0.8 to about 1.2% by weight. Particularly preferred preservatives are methylparaben, propylparaben, disodium edetate, 2-phenoxyethanol, imidazolidinyl urea and combinations thereof.

Minor adjunct ingredients may also be present in amounts each from 0.01 to 2%. These include antioxidants (e.g. butylated hydroxytoluene), antifoam agents, opacifiers and colorants, each in an effective amount to accomplish their respective functions.

The following examples will more fully illustrate the embodiments of this invention. All parts, percentages and proportions referred to herein and in the appended claims are by weight of the cosmetic composition unless otherwise indicated.

EXAMPLES

The following Table outlines a series of body lotions typical of compositions according to the present invention.

TABLE

| PHASE | COMPONENT | FORMULATIONS | | | | |
|---|---|---|---|---|---|---|
| | | 1 | 2 | 3 | 4 | 5 |
| A | Deionized Water | 63.09 | 59.09 | 64.69 | 63.59 | 59.09 |
| A | Disodium Edetate | 0.05 | 0.05 | 0.05 | 0.05 | 0.05 |
| A | Propylene Glycol | 2.40 | 2.40 | 2.40 | 2.40 | 2.40 |
| A | Methylparaben | 0.30 | 0.30 | 0.30 | 0.30 | 0.30 |
| A | Propylparaben | 0.10 | 0.10 | 0.10 | 0.10 | 0.10 |
| B | Triceteareth-4-Phosphate | 0.50 | 0.50 | 0.50 | 0.50 | 0.50 |
| B | Promulgen D® (Ceteareth-20/Cetearyl Alcohol) | 2.00 | 2.00 | 2.00 | 2.00 | 2.00 |
| B | Isopropyl Myristate | 6.70 | 8.70 | 5.10 | 6.70 | 6.70 |

TABLE-continued

| PHASE | COMPONENT | FORMULATIONS | | | | |
|---|---|---|---|---|---|---|
| | | 1 | 2 | 3 | 4 | 5 |
| B | Cetyl Alcohol | 1.44 | 1.44 | 1.44 | 1.44 | 1.44 |
| B | Glycerol Monostearate | 1.92 | 1.92 | 1.92 | 1.92 | 1.92 |
| B | Caprylic/Capric Triglyceride | 1.90 | 1.90 | 1.90 | 1.90 | 1.90 |
| B | Di-$C_{12}$-$C_{15}$ Alkyl Fumarate | 1.00 | 3.00 | 1.00 | 0.50 | 5.00 |
| B | Silicone Fluid 200 | 0.96 | 0.96 | 0.96 | 0.96 | 0.96 |
| B | Dow Corning® 3225C | 0.48 | 0.48 | 0.48 | 0.48 | 0.48 |
| C | 2-Phenoxyethanol | 0.70 | 0.70 | 0.70 | 0.70 | 0.70 |
| D | Carbopol® 934 (2% in deionized water) | 12.00 | 12.00 | 12.00 | 12.00 | 12.00 |
| E | Triethanolamine (99%) | 0.36 | 0.36 | 0.36 | 0.36 | 0.36 |
| E | Deionized Water | 1.00 | 1.00 | 1.00 | 1.00 | 1.00 |
| F | Butylated Hydroxytoluene | 0.10 | 0.10 | 0.10 | 0.10 | 0.10 |
| F | Fragrance | 3.00 | 3.00 | 3.00 | 3.00 | 3.00 |

The above compositions are prepared by heating Phase A ingredients to 70°–75° C. while homogenizing within a reactor. In a separate vessel, Phase B components (except Silicone Fluid 200 and Dow Corning® 3225) are heated to 70°–75° C. while mixing. Just prior to transfer, Silicone Fluid 200 and Dow Corning® 3225C are added to the Phase B vessel maintaining temperature at 70°–75° C.

Phase B is transferred to Phase A with homogenization. Temperature is maintained at 70°–75° C. for 15 minutes. Thereafter, the combination is slowly cooled to 60° C. Phase C is then added at 55°–60° C. and the combination mixed thoroughly. Phase D is added and mixed thoroughly. Phase E is added and mixed thoroughly at 40°–45° C. Thereafter, Phase F is added and mixed thoroughly at 40°–45° C. It is then cooled to 30°–32° C.

Although this invention is described with reference to specific Examples, it will be apparent to one skilled in the art that various modifications may be made thereto which fall within the spirit and purview of this invention.

What is claimed is:

1. A cosmetic composition comprising:
   (i) from about 0.5 to about 5% by weight of a fragrance;
   (ii) from about 50 to about 95% by weight of water;
   (iii) from about 0.1 to about 10% of a crosslinked polyacrylate or polyacrylic acid;
   (iv) from about 0.1 to about 40% of an oil selected from the group consisting of $C_8$–$C_{20}$ fatty acid monoesters, glycerides, silicones and combinations thereof;
   (v) from about 0.1 to about 10% of a di-$C_{12}$-$C_{15}$ alkyl fumarate having a melting point from about 35° to about 45° C.;
   (vi) from about 0.1 to 5% of an alkyl ether phosphate; and
   (vii) wherein the oil further comprises from 1 to 90% of isopropyl myristate and from 1 to 90% of capric/caprylic triglyceride, each by weight of total oil present in the composition.

2. A composition according to claim 1 wherein the phosphate is triceteareth-4-phosphate.

3. A composition according to claim 1 wherein the fragrance has a scent identical to a scent of a commercial signature perfume.

4. A composition according to claim 1 wherein the fragrance is formed of components selected from the group consisting of $C_{10}$–$C_{30}$ terpenes, $C_5$–$C_{50}$ aldehydes, $C_5$–$C_{50}$ ketones, $C_5$–$C_{50}$ esters and combinations thereof.

* * * * *

UNITED STATES PATENT AND TRADEMARK OFFICE
CERTIFICATE OF CORRECTION

PATENT NO. : 5,525,588
DATED : June 11, 1996
INVENTOR(S) : Michetti

It is certified that error appears in the above-indentified patent and that said Letters Patent is hereby corrected as shown below:

Title page, item [73],
Please change Assignee from "Elzabeth Arden Co.," to

-- Elizabeth Arden Co., Division of Conopco, Inc. --.

Signed and Sealed this

Twenty-sixth Day of November 1996

Attest:

BRUCE LEHMAN

*Attesting Officer*    *Commissioner of Patents and Trademarks*